United States Patent [19]

Iida

[11] Patent Number: 4,791,304

[45] Date of Patent: Dec. 13, 1988

[54] METHOD AND APPARATUS FOR SCANNING A WEB MATERIAL IN THE DIRECTION OF ITS WIDTH

[75] Inventor: Akihisa Iida, Shizuoka, Japan

[73] Assignee: Fuji Photo Film Co., Ltd., Kanagawa, Japan

[21] Appl. No.: 61,954

[22] Filed: Jun. 15, 1987

[30] Foreign Application Priority Data

Jun. 13, 1986 [JP] Japan ................................ 61-137666

[51] Int. Cl.$^4$ ............................................... H01J 3/14
[52] U.S. Cl. ...................................... 250/563; 250/236
[58] Field of Search ............... 250/562, 563, 572, 234, 250/235, 236; 356/430, 431, 444; 358/293, 294; 350/6.6, 6.7, 6.8, 6.9, 6.91

[56] References Cited

U.S. PATENT DOCUMENTS

| | | | |
|---|---|---|---|
| 4,173,441 | 11/1979 | Wolf | 356/431 |
| 4,268,172 | 5/1981 | Blitchington | 356/431 |
| 4,314,154 | 2/1982 | Minoura et al. | 358/293 |
| 4,460,273 | 7/1984 | Koizumi et al. | 250/563 |
| 4,468,120 | 8/1984 | Tanimoto et al. | 250/572 |
| 4,507,564 | 3/1985 | Shimada | 250/563 |
| 4,587,531 | 5/1986 | Dangler | 358/293 |

Primary Examiner—David C. Nelms
Assistant Examiner—William L. Oen
Attorney, Agent, or Firm—Young & Thompson

[57] ABSTRACT

A method of scanning a web material and an apparatus for use in the method in which a web material is spatially divided into smaller divisions in a scanning direction while being scanned in the direction of a width thereof with a scanning beam moved by means of a polyhedral mirror with a constant speed of rotation. Clock pulses from a pulse generator are counted up by a counter to access division data in a storing means to provide division signals according to which the width of the web material is spatially divided in the scanning direction.

7 Claims, 3 Drawing Sheets

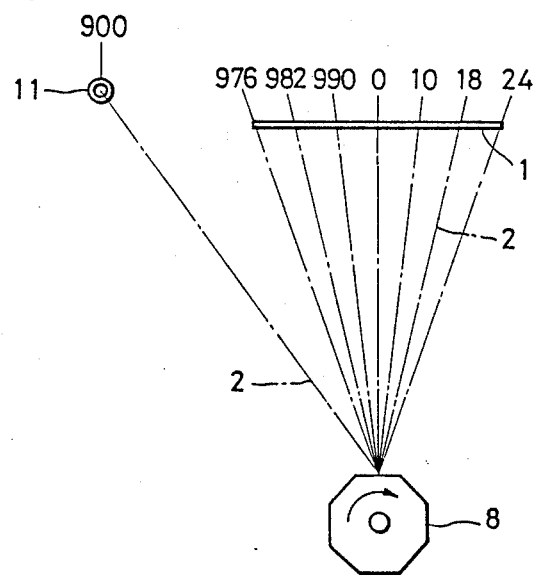

METHOD AND APPARATUS FOR SCANNING A WEB MATERIAL IN THE DIRECTION OF ITS WIDTH

BACKGROUND OF THE INVENTION

The present invention relates to a method and apparatus for scanning a web material with a light beam, and more particularly to a scanning method and apparatus in which a web material being scanned is spatially divided into smaller sections in the direction of the width thereof.

Various methods and apparatus are well known for scanning a surface of a web material with a scanning beam in the direction of the width of the web material to detect surface defects of the web material. The detection of surface defects is effected on the basis of a light intensity fluctuation of the scanning beam either reflected by or transmitted through the web material. In the above-mentioned scanning method and apparatus, a rotary polyhedral mirror is generally used to move the scanning beam transversely over the web material from edge to edge. In such scanning method and apparatus, it is practically necessary to specify a transverse location of surface defect on the web material. For this reason, it is usual to divide spatially the surface of the web material into smaller sections in the direction of the width of the web material and to specify the location of a surface defect on the web material based on that section in which an excessive fluctuation of light intensity of the scanning beam occurs. In order to divide spatially the surface of the web material into smaller sections in the direction of the width thereof, it is heretofore usual to use clock pulses into which a series of standard pulses generated at a constant pulse repetition frequency is divided. With the aid of the clock pulses, the output in the form of light intensity distribution of the scanning beam is periodically spatially divided.

Alternatively, a single light beam is divided into two, namely a scanning beam and a reference beam, by means of a beam splitter such as a half mirror well known per se disposed between a rotary polyhedral mirror and a web material to be scanned. The reference beam is detected by means of a linear arrangement of a plurality of light detecting elements while the scanning beam scans the surface of the web material in the direction of the width thereof. The outputs from the light detecting elements divide an output in the form of the light intensity distribution of the scanning beam, thereby dividing spatially the surface of the web material in the direction of the width of the web material.

A problem of the conventional scanning methods and apparatus in which a rotary polyhedral mirror is used is that, as is well known to those skilled in the art, the scanning beam travels on the surface of a web material being scanned in the direction of the width of the web material at a varying speed of movement. It is, therefore, usual to use an fθ lens in order to make the scanning beam travel in the direction of the width of the web material at a constant speed of movement. The usage of such an fθ lens is disclosed in, for example, Japanese Laid-Open Utility Model No. 58-120,913; or "OPTICS", Vol 10, No. 5, October, 1981, especially "Optical Design of Laser Scanning Lens", by K. Minoura et al., page 348.

However, the provision of an fθ lens makes the scanning apparatus complex not only in construction but also in adjustment, and hence expensive. In addition, the scanning apparatus with an fθ lens cannot divide a web material being scanned into smaller divisions with different distances due to the use of clock pulses divided at a regular pulse repetition period.

On the other hand, the scanning apparatus in which the reference beam is used to divide the width of a web material being scanned into smaller sections requires the provision of light detectors as many in number as the number of the smaller sections to be divided. In addition, the use of the beam splitter for producing the scanning and reference beams from a single beam results in a reduced power of the scanning beam. For this reason, it is required to use a high power beam generator. This requirement, however, makes the scanning apparatus expensive and complex in construction.

OBJECT OF THE INVENTION

It is, therefore, an object of the present invention to provide a method and apparatus for scanning a web material by using a polyhedral mirror in which the width of the web material being scanned is spatially divided into smaller sections.

It is another object of the present invention to provide a method and apparatus for scanning a web material by using a polyhedral mirror in which the width of the web material is spatially divided into smaller sections either with regular intervals or with different intervals.

It is still another object of the present invention to provide an apparatus for scanning a web material by using a polyhedral mirror which is simple in construction.

SUMMARY OF THE INVENTION

In accordance with the present invention, a scanning apparatus in which a scanning beam is moved on a surface of a web-like material being scanned over its width by means of a polyhedral mirror with a constant speed of rotation, comprises means for storing division data; means for generating a series of clock pulses; means disposed at a reference position from which scanning starts for detecting the light beam to provide a trigger signal; means actuated by the application of the trigger signal thereto for counting up the clock pulses to provide address signals, one for each of the clock pulses, to the storing means to read out the division data; and means for providing division signals corresponding to the division data in order to divide spatially the width of the web material being scanned into smaller sections. In each storage location of the storing means, the division data of logic "0" or logic "1" is preliminarily stored. When, for example, the data of logic "1" is read out, a division signal is provided so as to define spatially a first section of the width of the web material.

According to a feature of the present invention, although the polyhedral mirror rotates at a constant speed and causes a scanning beam to travel at a varying speed of movement on the surface of the web material in the direction of the width of the web material, the web material can be spatially divided into either equidistant or inequidistant sections in the direction of the width of the web material without the provision of optical elements such as an fθ lens or a beam splitter which makes the scanning apparatus complicated in construction and in adjustment. Even without constant speed of movement of the scanning beam over the surface, the scanning apparatus can divide spatially the width of the web material into equidistant sections.

BRIEF DESCRIPTION OF THE DRAWINGS

These and other objects and features of the present invention will be described in more detail in the following; by way of example, reference being had to the accompanying drawings, in which:

FIG. 2 is a conceptional illustration showing the PROM of FIG. 1;

FIG. 3 is an illustration showing the scanning of web material which is shown in section;

DETAILED DESCRIPTION OF THE INVENTION

Although this description will be directed to a scanning method and apparatus of the type having a scanning beam which is transmitted through a web material to scan the same, the present invention is equally applicable to a scanning method and apparatus of the type having a scanning beam which is reflected from a web material to scan the same.

Figure 1:
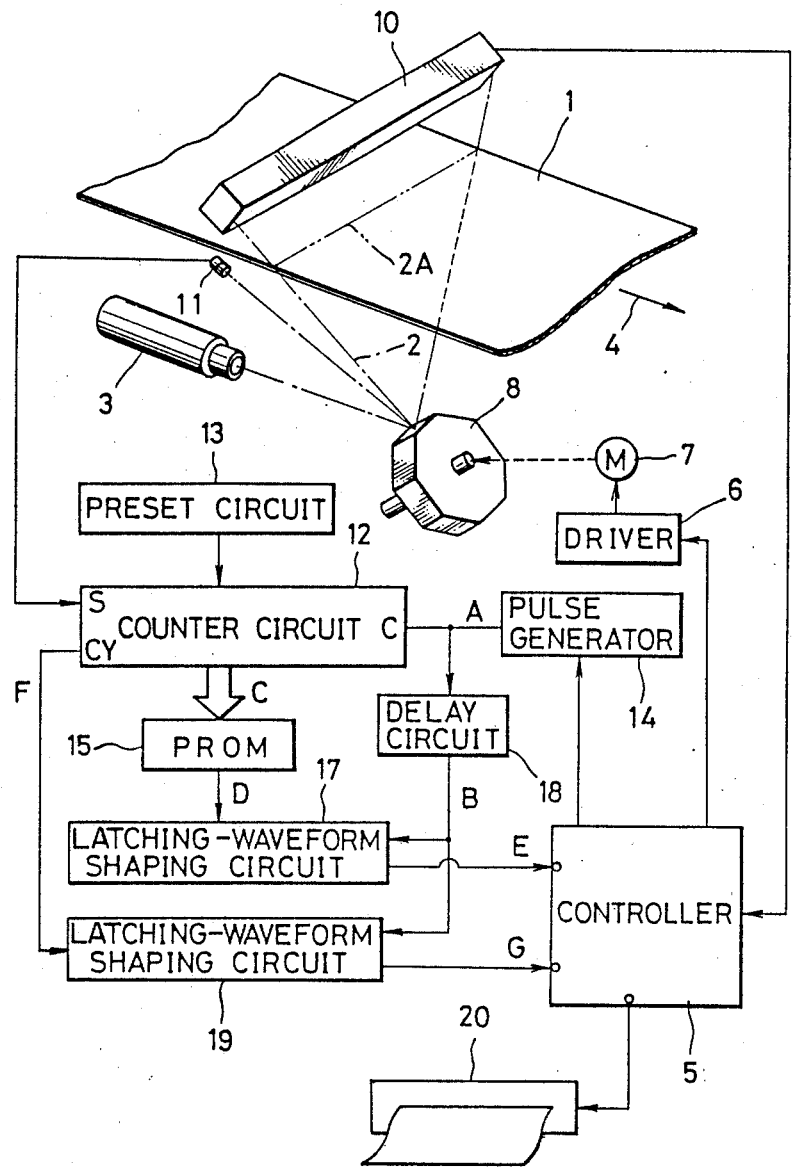
FIG. 1 is a diagram showing a scanning apparatus according to the present invention.

Referring now to FIG. 1 showing a surface inspection apparatus to which the present invention is applied, a web material 1 to be inspected is translated slowly but at a constant speed of movement in a direction shown by an arrow 4. During movement of the web material 1, a laser beam 2 scans the under surface of the web material 1 transversely, namely in the direction of the width of the web material 1, from left to right as seen in FIG. 1. The laser beam 2, which is generated by a laser radiation source 3, is reflected by one of mirror surfaces of a polyhedral mirror 8 rotating clockwise as seen in FIG. 1 at a constant high speed and is directed to the under surface of the web material 1. The reflected laser beam 2 moves along a line 2A notionally depicted for easy understanding, as a result of the rotation of the polyhedral mirror 8 which is caused by a motor 7 under the control of a controller 5 and a driver 6.

Beyond the line 2A, a light detector 10 extending along a facing the line 2A is disposed so as to receive the laser beam 2 transmitted through the modulated in intensity by the web material 1 in order to provide an electric output, which is in proportion to the light intensity of the laser beam received, to the controller 4. If there is any surface defect such as a jog, a dent, an unevenness or an undulation with an undue thickness in comparison with a prescribed thickness, the output from the light detector 10 will fluctuate in magnitude. When the fluctuation exceeds predetermined limits, the web material is estimated to have an unallowable defect on the surface.

Disposed out of the path of the web material 1 is a light detector 11 at a reference position from which scanning starts. When the light detector 11 detects the laser beam 2, it provides a trigger signal which in turn is applied to and actuates a counter circuit 12 to count up pulses from a pulse generator 14 described later. The presence of a trigger signal at a terminal S of the counter circuit 12 sets the initial count value of the counter circuit 12 to an initial count value, for example, "900" (nine hundred) which is preliminarily set in a preset circuit 13.

The counter circuit 12 starts to count up clock pulses supplied to its terminal C from the pulse generator 14 at the moment that the trigger signal is supplied thereto. Consequently, the counter circuit 12 increases the counted value starting from the initial value of "900" one by one. Each counted value is used as an access signal C in association with each of addresses of storage locations of PROM 15. PROM 15, which is conceptionally illustrated in FIG. 2, has storage locations consecutively addressed by "0" (zero) to "999". In each storage location, a binary signal, logic "1" or logic "0", is stored. The counter circuit 12 is adapted to reset its count to "0" (zero) with the first application of a clock pulse from the pulse generator 14 after the counter circuit 12 has counted a value of "999" and simultaneously to provide a carry pulse F at its terminal CY. At this moment, a location to be accessed is changed from the storage location of the address of "999" to that of the address of "0".

The allotment of the binary signals of logics "0" and "1" in PROM 15 is done in such a way to write the binary signal of logic "1" in the storage locations of the addresses of "0", "10", "18", "24", "976", "982" and "990" if the surface of the web material 1 is divided into six equidistant sections in its transverse direction as is shown in FIG. 3. In greater detail: because the laser beam 2 travels on the surface of the web-like material 1 at a varying speed of linear movement in spite of the polyhedral mirror 8 rotating at a constant speed, the closer the laser beam 2 gets to the center of the web material 1, the faster it scans. It is therefore necessary to allot a larger number of clock pulses to an outer section of the web than to an inner section, when dividing the web material 1 in the direction of the width thereof into equidistant smaller sections. It will be understood by those skilled in the art that the number of locations to store the binary signal of logic "1" is decided considering such factors as the distance between the web material 1 and the rotary polyhedral mirror 8, the number of smaller sections into which the web material 1 is to be spatially divided in the direction of the width thereof, the speed of rotation of the polyhedral mirror 8, and so forth.

The scanning of the web material 1 with the laser beam 2 is effected from left to right in FIG. 3. In order to detect the commencement of scanning, the light detector 11 is disposed at a predetermined distance from the left side edge of the web material 1 which is designated as a reference position from which scanning starts. If it is assumed that seventy-six (76) pre-scanning clock pulses are required for the rotation of the polyhedral mirror 8 through an angle sufficient to allow the laser beam 2 to travel from the reference position to the left side edge of the web material 1, the preset circuit 13 must be preset to the value of "900" which in turn is transferred to the counter circuit 12 upon the application of the trigger signal from the light detector 11. It will be apparent to those skilled in the art that, if the light detector 11 is placed at a different reference position, a different value must be preset in the preset circuit 13 in accordance with the different distance between the reference position of the light detector 11 and the left side edge of the web material 1. For a distance of fifty-five (55) pre-scanning clock pulses, for instance, the initial value of the preset circuit 13 is preset to the value of "920".

Figure 4:
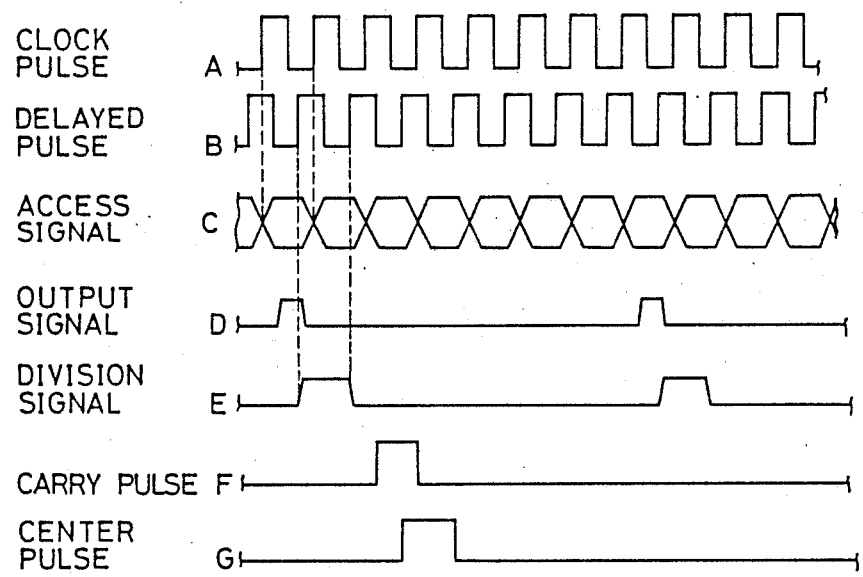
FIG. 4 shows waveforms of signals from various operation elements of FIG. 1.

When all the operational units are actuated to work under the control of the controller 5, the light detector 11 at a predetermined reference position detects the laser beam 2 from the laser radiation source 3 to provide a trigger signal to the counter circuit 12, setting the initial value of the counter circuit 12 to the value of "900" which is preliminarily set in the preset circuit 13. Simultaneously, the counter circuit 12 starts to count up clock pulses A of rectangular waveform as shown in FIG. 4, from the pulse generator 14, increasing its counted value one by one, from "901" to "999". Each counted value of the counter circuit 12 is transferred as an access signal C shown in FIG. 4 to address the corresponding storage location of PROM 15 so as to read its stored date (binary signal of logic "0" to logic "1") out in real time. If in fact the data read out is the binary signal of logic "0", the PROM 15 keeps its output at low level.

At the moment the counter circuit 12 counts up seventy-six clock pulses after the application of the trigger signal thereto, namely, the counted value of the counter circuit 12 reaches the value of "976", PROM 15 is accessed by the address of "976" to output the stored data, which is the binary signal of logic "1", which in turn is transferrd as an output signal D in the form of trapezoidal pulse as is shown in FIG. 4 to a latching-waveform shaping circuit 17. Supplied also to the latching-waveform shaping circuit 17 is a rectangular pulse train supplied from the pulse generator 14 but delayed by means of a delay circuit 18 as is shown in FIG. 4. Each delayed pulse B serves to shape the waveform of the output signal D from PROM 15 and to hold the waveform-shaped output signal D for a pulse repetition period of the delayed pulse train. The output signal D thus waveform-shaped is provided as a division signal E to the controller 5. Such a division signal E is provided every time the predetermined value, namely "976", "982", "990", is counted by the counter circuit 12. Therefore, three division signals can be produced in total until the counted value "999" is reached.

The counter circuit 12 is adapted to reset its counted value to "0" (zero) with the first clock pulse A after having reached to the predetermined end value of "999" so as to provide a carry pulse F to the latching-waveform shaping circuit 19 which can function in the same way as the latching-waveform shaping circuit 17. The carry pulse F is waveform-shaped and held for a pulse repetition period of the delayed pulses B, and then output as a center pulse G which in turn is transmitted to the controller 5. It should be noted here that when the center pulse G is transmitted to the controller 5, the laser beam 2 lies just on the center of the width of the web material 1. As is apparent from FIG. 2, since, when the count of the counter circuit 12 is set to "0" (zero), the data read out from PROM 15, specifically the storage location addressed by "0" (zero), is the binary signal of logic "1", a division signal E is provided to the controller 5.

After the counter circuit 12 has been set to the value of "0" (zero), the counter circuit 12 restarts to count up clock pulses. In the same way as described previously, the division signal E is provided every time the counter circuit 12 counts each of the predetermined values of "10", "18", and "24". Therefore, three division signals are provided in total until the counted value of "900" is reached. Consequently, during the time the laser beam 2 travels over the whole width of the web material 1, seven division signals E are provided so as to divide the width of the web material 1 into six smaller sections. Because the timing with which the division signal E is provided depends on the allocation of the binary signal of logic "1", the equidistant divisions are easily effected in spite of the varying speed of movement of the laser beam 2 on the web material 1. In addition, it is easy not only to increase or decrease the number of divisions but also to divide inequidistantly as is required.

Figure 5:
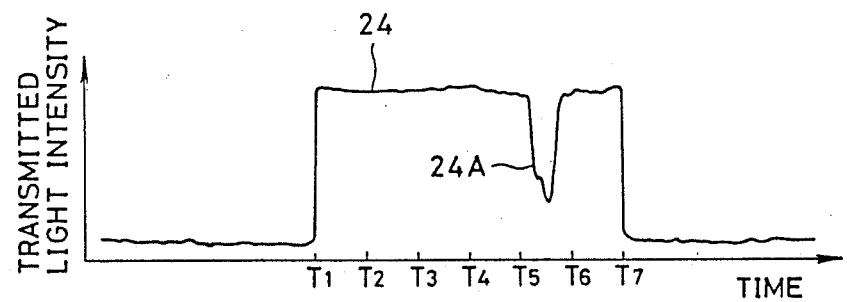
FIG. 5 is a graph of light intensity of a scanning beam transmitted through a web material.

As is shown in FIG. 1, as an output unit for the controller 5, there is a printer 20 connected to the controller 5 to print the output in the form of a light intensity distribution curve 24 of the laser beam 2 (see FIG. 5) transmitted through the web material 1 to the light detector 10. Simultaneously with the printing of the waveform of light intensity distribution, there are plotted on X-axis the times T1 to T7 at which the division signals E are produced. Along the curve 24 of the light intensity distribution, a fluctuation 24A which means a defect exists at about time T5 between the times T1 and T7. Upon printing the waveform of light intensity distribution, the output of the light detector 10 and the division signals F are temporarily stored in a buffer memory until the passage of the laser beam 2A between the edges of the web material 1 is completed.

It should be understood that as the repetition period of the binary signal of logic "1" can be desirably determined, it is easy to increase or decrease the number of spatial divisions either with equidistant intervals or with inequidistant intervals by selectively using different PROMS wherein different division data are preliminarily stored. From the practical point of view, it is advantageous to close the spatial divisions at any part of the surface of the web material where defects are liable to occur.

Although the present invention has been fully described by way of the preferred embodiments thereof with reference to the accompanying drawings, it is to be noted that the possibility of making various changes and modifications will be apparent to those skilled in the art. Therefore, unless otherwise such changes and modifications depart from the true scope of the present invention, they should be construed as included therein.

What is claimed is:

1. A method of scanning a web material in the direction of the width of said web material with a light beam moved by means of a polyhedral mirror with a constant speed of rotation in which said web material is spatially divided into smaller divisions in said scanning direction, said method comprising the steps of
producing a series of clock pulses;
detecting said light beam at a reference position from which scanning starts to actuate a counter to count up said series of clock pulses; and
accessing division data stored in a storing means with counted values of said series of clock pulses by said counter to provide division signals, said division data being accessed by progressively more clock pulses as said light beam moves toward the center of said web material and by progressively fewer clock pulses as said light beam moves away from the center of said web material, whereby said web material is spatially divided into said smaller divisions in said scanning direction.

2. A method as defined in claim 1, wherein said division data comprises binary signals.

3. A method as defined in claim 1, wherein said divisions are inequidistant.

4. A method as defined in claim 1, wherein said divisions are equidistant.

5. An apparatus for scanning a web material in the direction of the width of said web material with a light beam moved by means of a polyhedral mirror with a constant speed of rotation in which said web material is spatially divided into smaller divisions in said scanning direction, said aparatus comprising means for storing division data;

means for producing a series of clock pulses;

means disposed at a reference position from which scanning starts for detecting said light beam to provide a trigger signal;

means actuated by said trigger signal for counting up said series of clock pulses to access said division data with counted values of said series of clock pulses, said division data being accessed by progressively more clock pulses as said light beam moves toward the center of said web material and by progressively fewer clock pulses as said light beam moves away from the center of said web material, thereby providing division signals according to which said web material is spatially divided into smaller divisions in said scanning direction.

6. An apparatus as defined in claim 5, wherein said storing means is replaceable with another one in which different division data is stored.

7. An apparatus as defined in claim 5, wherein said storing means is a PROM.

* * * * *